US00PP12397P2

(12) United States Plant Patent
Heims

(10) Patent No.: US PP12,397 P2
(45) Date of Patent: Feb. 5, 2002

(54) TIARELLA PLANT NAMED 'SPRING SYMPHONY'

(75) Inventor: Dan M. Heims, Portland, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/324,624

(22) Filed: Jun. 2, 1999

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Anne Marie Grünberg
(74) *Attorney, Agent, or Firm*—Klarquist Sparkman, LLP

(57) ABSTRACT

A new and distinct hybrid of Tiarella plant characterized by unique compact form, distinctive foliage shape and outstanding bloom color.

1 Drawing Sheet

The present invention relates to a new and distinct hybrid of Tiarella, which originated as a cross-pollination of Tiarella 'Pink Bouquet' (pollen parent) (unpatented) and an unnamed Tiarella seedling 97-7 (seed parent) (unpatented) in the Saxifrage family. Due to the fact that the parents are from interspecific crosses and several species are involved, no species designations can be given. The new variety has been reproduced only by asexual propagation (division and tissue culture). Each of the progeny exhibits identical characteristics to the original plant.

This plant is characterized by the following:

1. Unique compact form.
1. Distinctive small, well-marked foliage.
3. Outstanding bloom color.

Asexual propagation by division and tissue culture as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPH

The FIGURE is a picture of Tiarella "Spring Symphony" in bloom in April in Canby, Oreg.

DETAILED PLANT DESCRIPTION

The following is a detailed description of the new Tiarella hybrid based on observations of two year old specimens grown in a cool greenhouse in Canby, Oreg. The color descriptions are all based on The Royal Horticultural Society Colour Chart.

Plant:

*Form and hardiness.*—Herbaceous perennial; retains foliage in USDA hardiness Zones 5 and above, dies back in USDA hardiness zones 3 and 4.

*Habit.*—Clumping.

*Size.*—To 25 cm wide and 17.5 cm high.

Foliage:

*Shape.*—Palmate, deeply 5–7 lobed, terminal lobe the longest, irregularly toothed. The lobes below the terminal are often constricted near the lobe base giving a unique shape.

*Length.*—5.5–7 cm.

*Width.*—7–8 cm.

*Petiole length.*—12.5–16 cm.

*Margins.*—Incised.

*Apex.*—Apiculate.

*Base.*—Hastate.

*Texture.*—Hispid (upper surface).

*Leaf arrangement.*—Basal clump.

*Venation.*—Palmate.

Flower:

*Parts.*—5 petals, 5 calyx lobes, 10 stamens, pollen color is RHS 28A Orange Group.

*Petal shape.*—Triangular, clawed.

*Flower type.*—Complete, calyx tube campanulate, ovary superior.

*Flower size.*—0.50–0.70 cm wide.

*Flower number.*—42–52 blooms per raceme.

*Peduncle width.*—About 2 mm.

*Blooming habit.*—Simple upright raceme to 21–23 cm. high and 1.5 cm wide. One bract. 70–85 racemes at one time per second year plant.

*Bloom period.*—April to May. Minor sporadic rebloom in fall. Individual racemes are in color for 10 days.

*Fragrance.*—Slight fragrance.

Fruit:

*Type.*—A one-celled, horned capsule.

*Capsule.*—Beak-like, composed of 2 unequal parts.

*Fertile.*—Yes.

Disease tolerance: Excellent disease resistance to powdery mildew, the common problem of Tiarella.

Color characteristics:

*Foliage.*—Leaves are two-toned. They are mottled with RHS 187A Greyed Purple Group along each lobe's central vein, major lateral veins, and the leaf center. Spring/Summer upper surface: RHS 137A Green group. Note: two colors may be visible on the leaves of the same plant in spring. Coloration is dependent on the maturity of the leaf. Old over-wintered leaves show the color RHS 200A Brown Group and young new leaves are RHS 137A Green group. Winter color upper surface: RHS 200A Brown Group. Spring/Summer lower surface: RHS 147B Yellow-Green Group. Coloration of the leaf centers/mature leaves: RHS 187A Greyed Purple Group.

*Flowers.*—RHS 155B White Group, shading to RHS 56C Red Group. Buds are RHS 62B–D Red Purple Group.

*Peduncle.*—RHS 165A Greyed-Orange Group.

DESCRIPTION OF PARENT PLANTS

This Tiarella hybrid has characteristics that make it unique from its parents: Tiarella 'Pink Bouquet' has pink flowers and unmarked foliage of moderate size. Tiarella 'Spring Symphony' has small foliage that is well marked. Flower color is more intense in Tiarella 'Spring Symphony' than either parent. The seedling, Tiarella 97-7 that served as seed parent, has very fine leaves that are moderately marked, and moderately pink flowers.

I claim:

1. A new and distinct hybrid of Tiarella plant characterized by unique compact form, distinctive foliage shape and outstanding bloom color.

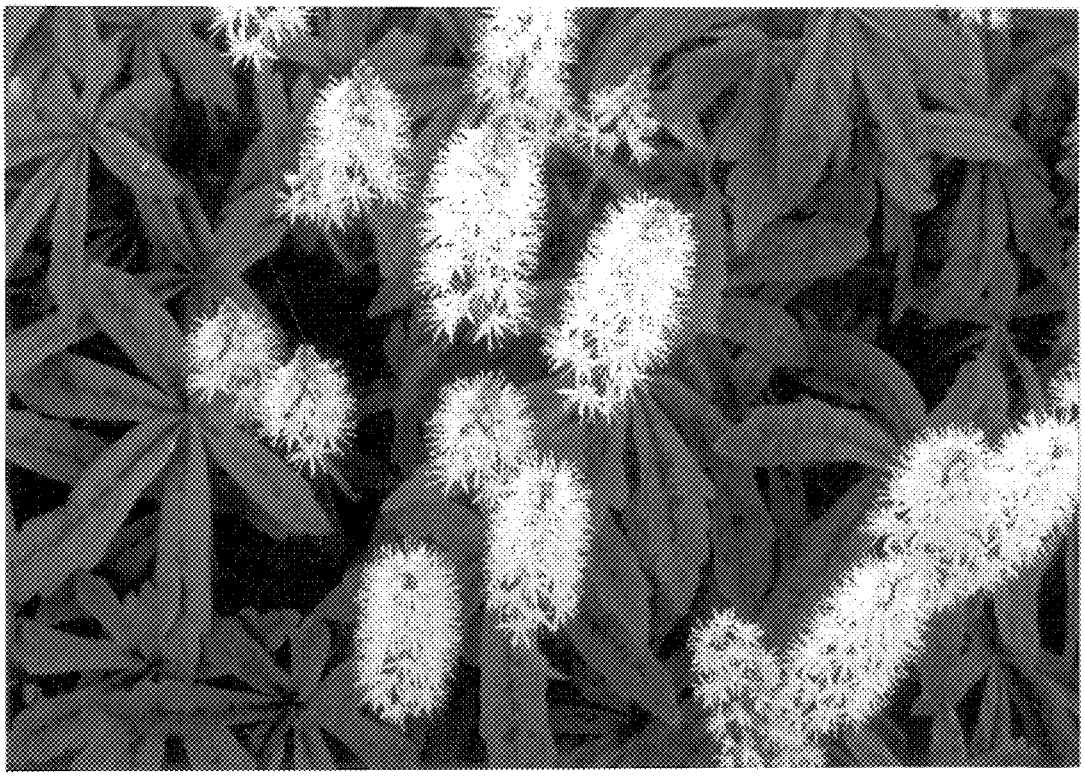

* * * * *